US 7,059,544 B2

(12) United States Patent
Leonard et al.

(10) Patent No.: US 7,059,544 B2
(45) Date of Patent: Jun. 13, 2006

(54) VORTEX GENERATOR FOR DISPENSING ACTIVES

(75) Inventors: Stephen B. Leonard, Franksville, WI (US); Daniel J. Plankenhorn, Milwaukee, WI (US); Ralph W. Oakeson, Boonton, NJ (US)

(73) Assignee: S.C. Johnson & Son, Inc., Racine, WI (US)

( * ) Notice: Subject to any disclaimer, the term of this patent is extended or adjusted under 35 U.S.C. 154(b) by 111 days.

(21) Appl. No.: 10/773,889

(22) Filed: Feb. 6, 2004

(65) Prior Publication Data

US 2004/0195351 A1 Oct. 7, 2004

Related U.S. Application Data

(60) Provisional application No. 60/445,240, filed on Feb. 6, 2003.

(51) Int. Cl.
*A62C 31/00* (2006.01)
*B05B 7/10* (2006.01)
*B05B 1/26* (2006.01)
*B05B 1/34* (2006.01)

(52) U.S. Cl. .......... 239/398; 239/399; 239/401; 239/402.5; 239/461; 239/463; 239/480

(58) Field of Classification Search ........ 239/398, 239/399, 401, 402.5, 461, 463, 480, 484, 239/494
See application file for complete search history.

(56) References Cited

U.S. PATENT DOCUMENTS

| 3,940,060 | A |   | 2/1976  | Veits             |
|-----------|---|---|---------|-------------------|
| 4,157,703 | A |   | 6/1979  | Brown et al.      |
| 4,534,914 | A |   | 8/1985  | Takahashi et al.  |
| 4,735,282 | A |   | 4/1988  | Lippold           |
| 5,100,242 | A | * | 3/1992  | Latto ........... 366/267 |
| 5,341,650 | A |   | 8/1994  | Nagasawa et al.   |
| 5,361,989 | A |   | 11/1994 | Merchat et al.    |
| 5,376,166 | A |   | 12/1994 | Hoffmann et al.   |
| 5,415,246 | A |   | 5/1995  | Cooper            |
| 5,429,650 | A |   | 7/1995  | Hoffmann et al.   |
| 5,474,059 | A |   | 12/1995 | Cooper            |
| 5,483,953 | A |   | 1/1996  | Cooper            |
| 5,823,434 | A |   | 10/1998 | Cooper            |
| 5,851,442 | A |   | 12/1998 | Spector           |
| 6,357,726 | B1|   | 3/2002  | Watkins           |

FOREIGN PATENT DOCUMENTS

| DE | 40 33 079    | 4/1992  |
|----|--------------|---------|
| JP | 01 005556    | 1/1989  |
| WO | WO 99/65550  | 12/1999 |
| WO | WO 00/53301  | 9/2000  |

* cited by examiner

Primary Examiner—Davis Hwu

(57) ABSTRACT

A vortex generator creates a waveform within a housing. The waveform evolves into a vortex as it exits an orifice of the housing. The vortex carries a bolus of active substances held within the housing. A different number of actives can be used. To form a waveform, the housing has a diaphragm with an actuator for moving the diaphragm. The housing may have a mechanism for facilitating directional pointing and/or causing oscillating movement of the housing to enable multi-directional targeting of the vortex.

11 Claims, 13 Drawing Sheets

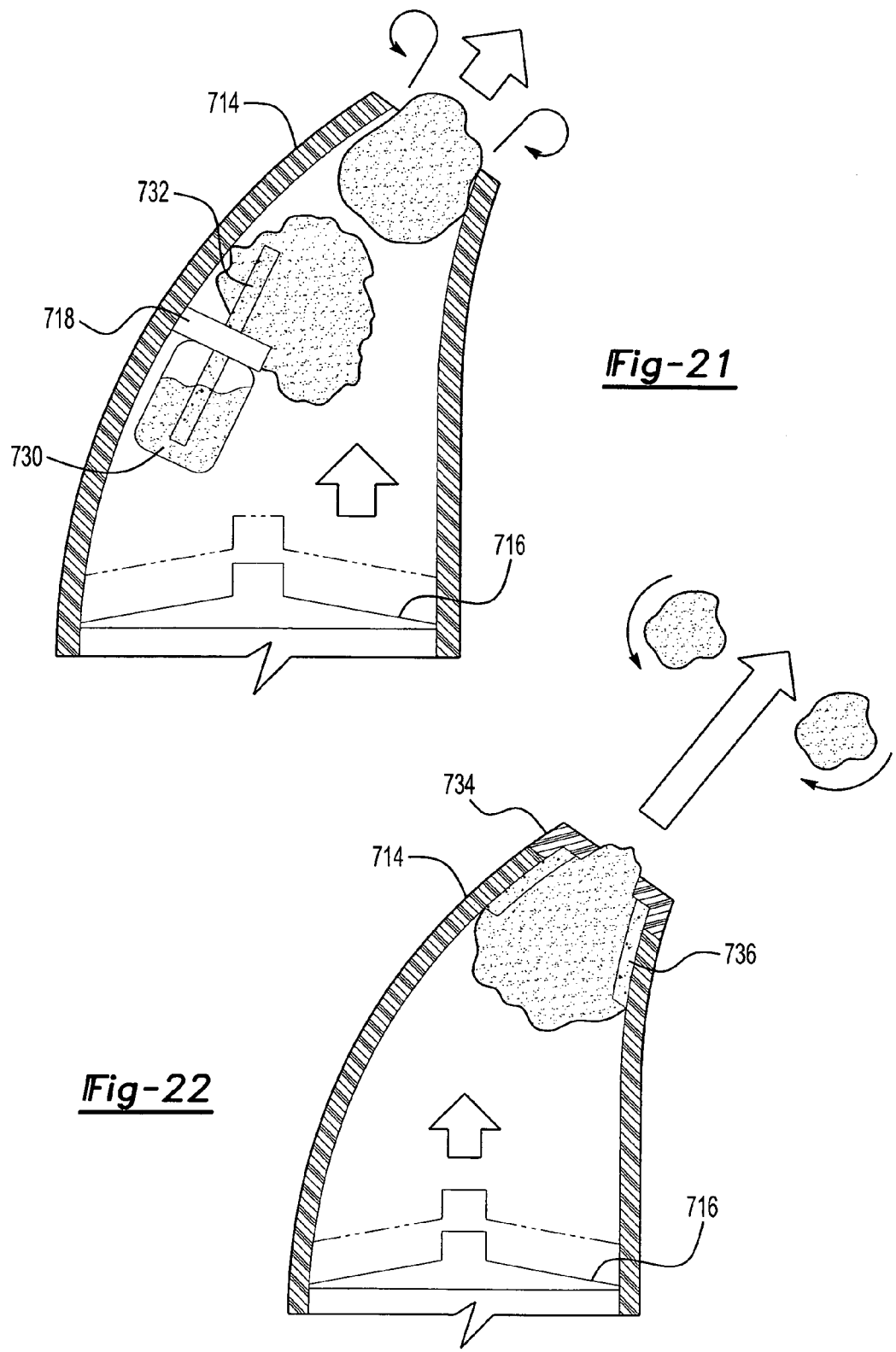

VORTEX GENERATOR FOR DISPENSING ACTIVES

This application claims the benefit of provisional application 60/445,240, filed Feb. 6, 2002.

FIELD OF THE INVENTION

The invention relates to a device for dispensing an active substance, such as a fragrance or insecticide, by generating a vortex.

BACKGROUND OF THE INVENTION

The ability to directionally and accurately target the dispensing of active substances is the desired goal of devices for dispensing such substances. Fans generating a fluid stream for carrying active substances have been used to dispense such substances. The fluid stream often lacks integrity and, while dispersing the active substance, does not always provide the ability to target an area remote from the origin.

Previous patents have disclosed the use of a vortex generator to deliver active substances. One such patent is U.S. Pat. No. 6,357,726 (Watkins) which discloses a system having a plurality of cartridges and a vortex delivering a bolus of scent in an air ring.

U.S. Pat. No. 5,823,434 (Cooper) discloses an aerosol dispensing apparatus having a speaker diaphragm mounted in the bottom of a housing. The apparatus generates a train of ring vortices exiting the apparatus through an orifice.

One aspect of the invention is to provide a vortex generator for dispensing active substances.

Another aspect of the invention to have a vortex generator that uses minimal energy to create a vortex.

A still further aspect of the invention to provide a targeted dispensing device.

It is yet another aspect of the invention to have an oscillating vortex generator.

SUMMARY OF THE INVENTION

A vortex generator creates a waveform within a housing. The waveform evolves into a vortex as it exits an orifice of the housing. The vortex carries a bolus of active substances held within the housing. A different number of actives can be used. To form a waveform, the housing has a diaphragm with an actuator for moving the diaphragm. The housing may have a mechanism for facilitating directional pointing and/or causing oscillating movement of the housing to enable multi-directional targeting of the vortex.

BRIEF DESCRIPTION OF THE DRAWINGS

FIG. 21 is a cross section view of the embodiment of FIG. 17 with a refill bottle;

FIG. 22 is a cross section view of the embodiment of FIG. 17 with a replaceable refill nozzle tip;

DETAILED DESCRIPTION OF THE INVENTION

Figure 1:
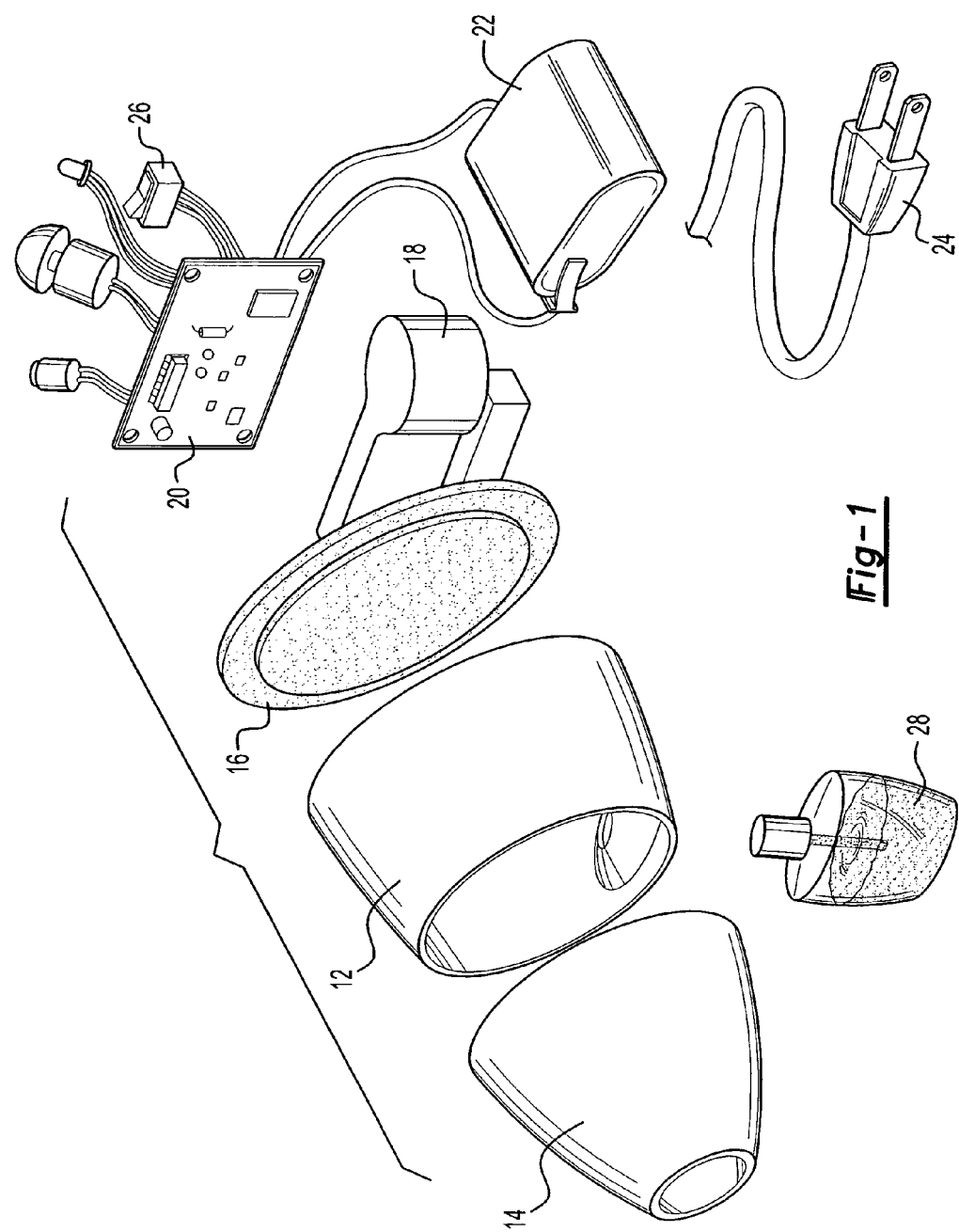
FIG. 1 is an exploded view of the elements needed for a vortex generating mechanism.

The essential parts of a vortex generator are depicted in FIG. 1. A vortex chamber has a diaphragm on one end and a vortex cone with an orifice on the opposite end. A diaphragm actuator causes movement of the diaphragm to induce a waveform in the vortex chamber. As the waveform travels through the vortex chamber and exits through the orifice in the vortex cone, the wave evolves into a vortex. Any airborne or gaseous substance within the vortex chamber will be entrained by an active substance held within the chamber to create a vortex bolus. The active substance usually contained in a refill 28, and is introduced into the vortex chamber in the manner described.

A diaphragm actuator 18 causes movement of the diaphragm 16. The diaphragm actuator needs both power and control signals. The power is provided by a disposable or rechargeable battery 22, photovoltaic cell, or standard power cord 24 plugged into a household outlet. Control signals are provided through a PC board to control the movement of the actuator. Controls 26 alter the PC board signals. The controls 26 are accessible to the user to allow the customizing of the actuator timing and, therefore, the disbursement of the substance within the vortex chamber.

Figure 2:
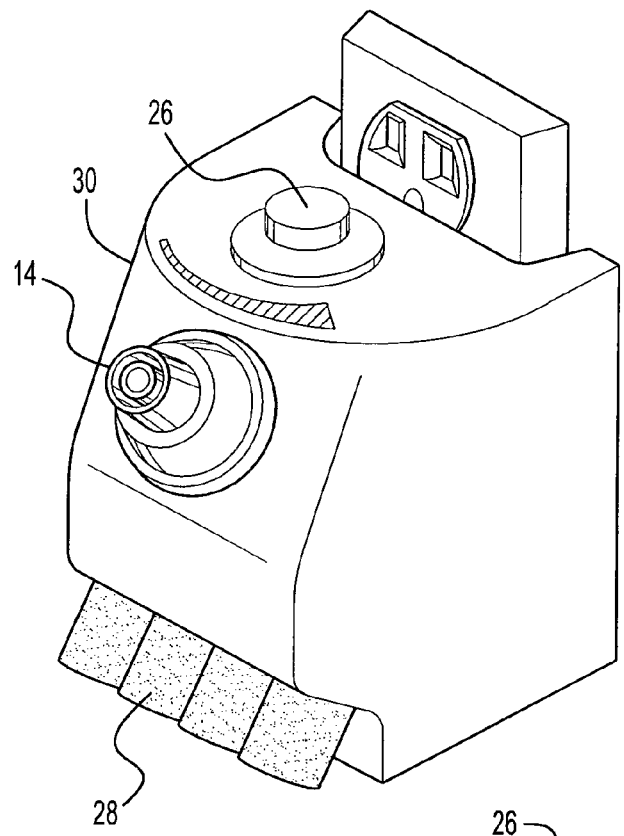
FIG. 2 is a perspective view of a complete vortex generating mechanism.
Figure 3:
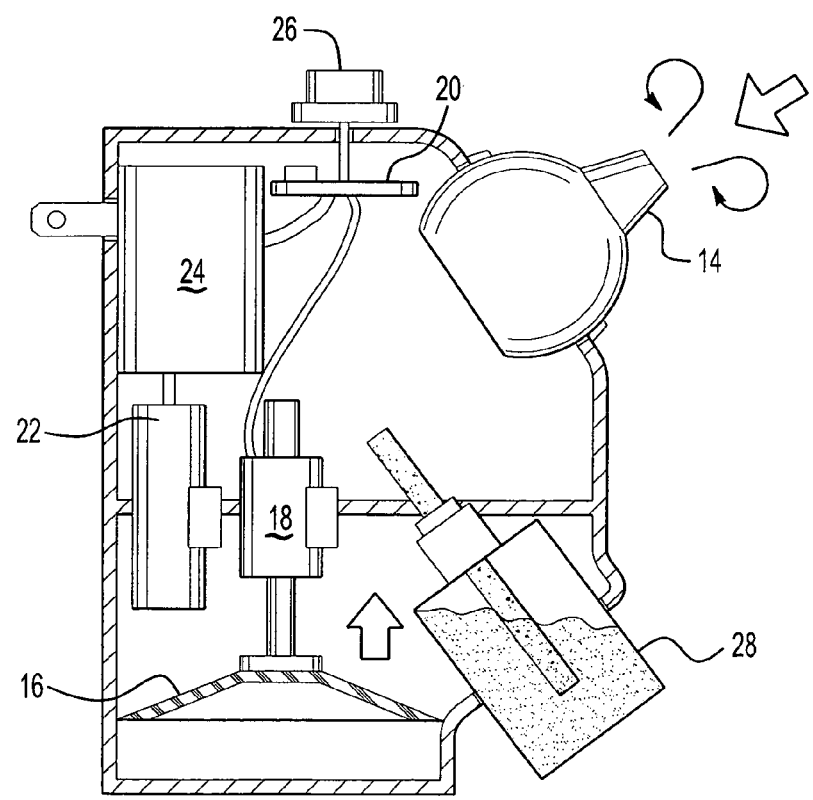
FIG. 3 is a cross-sectional view of the mechanism of FIG. 2.

FIG. 2 shows a perspective of a vortex generator having a housing 30. The vortex cone 14 is mounted on the front of the housing and controls 26 are easily accessible to the user to allow control of the vortex formation. The cross section of the vortex generator is seen in FIG. 3. The chamber formed by the housing 30 serves as a vortex chamber with the nozzle 14 serving as a vortex cone. Power supply 24 mounted to the inside of the housing allows the vortex generator to be connected to a household outlet. A diaphragm 16 situated within the housing separates the housing into two compartments. In the lower compartment, an actuator 18 causes movement of the diaphragm. The actuator 18 is connected a PC board 20 which receives power from the power cord 24 and is controlled by controls 26. A refill bottle 28 extends upwardly into the housing to release any active substance into the upper compartment of the housing.

Figure 4:
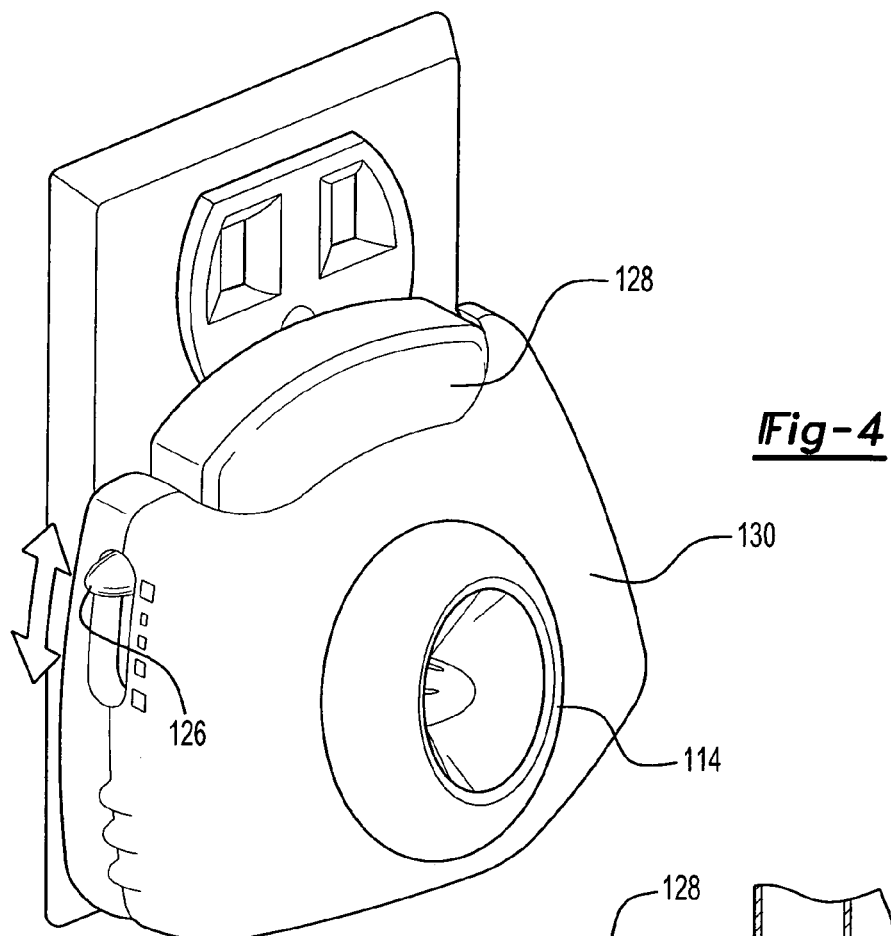
FIG. 4 is a perspective view of a second embodiment of a vortex generator.
Figure 5:
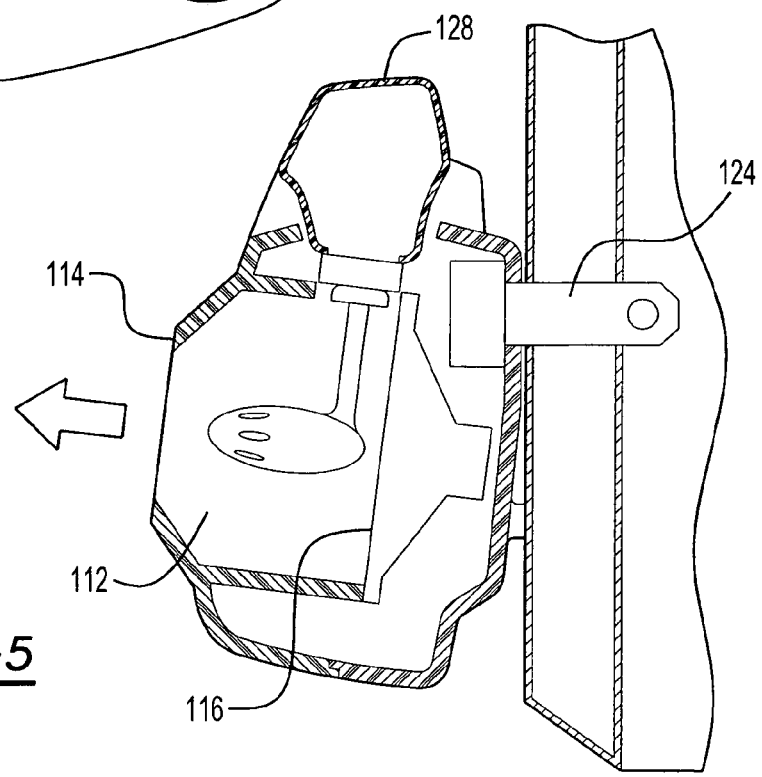
FIG. 5 is a cross-sectional view of the second embodiment shown in FIG. 4.

A second embodiment of the vortex generator is shown in FIG. 4 having a housing 130 receiving a refill 128 and having a vortex cone 114 on the front surface and controls 126 mounted on the side. A cross section of this second embodiment is seen in FIG. 5. Power supply 124 extends from the housing for engagement with a household outlet. The refill bottle 128 is suspended over the vortex chamber 112 and feeds an eminator within the chamber. A diaphragm 116 encloses one end of the chamber and the vortex cone 114 is located at the other end. It must be noted that the vortex cone can be provided of virtually any shape (conical, bevel, square, etc.) provided that the orifice in the cone is centrally located, and proportional to the diameter of the diaphragm. This is critical to generating an optimized vortex bolus. In the described embodiment, an ideal proportion of diaphragm area to orifice opening is 3:1.

Figure 6:
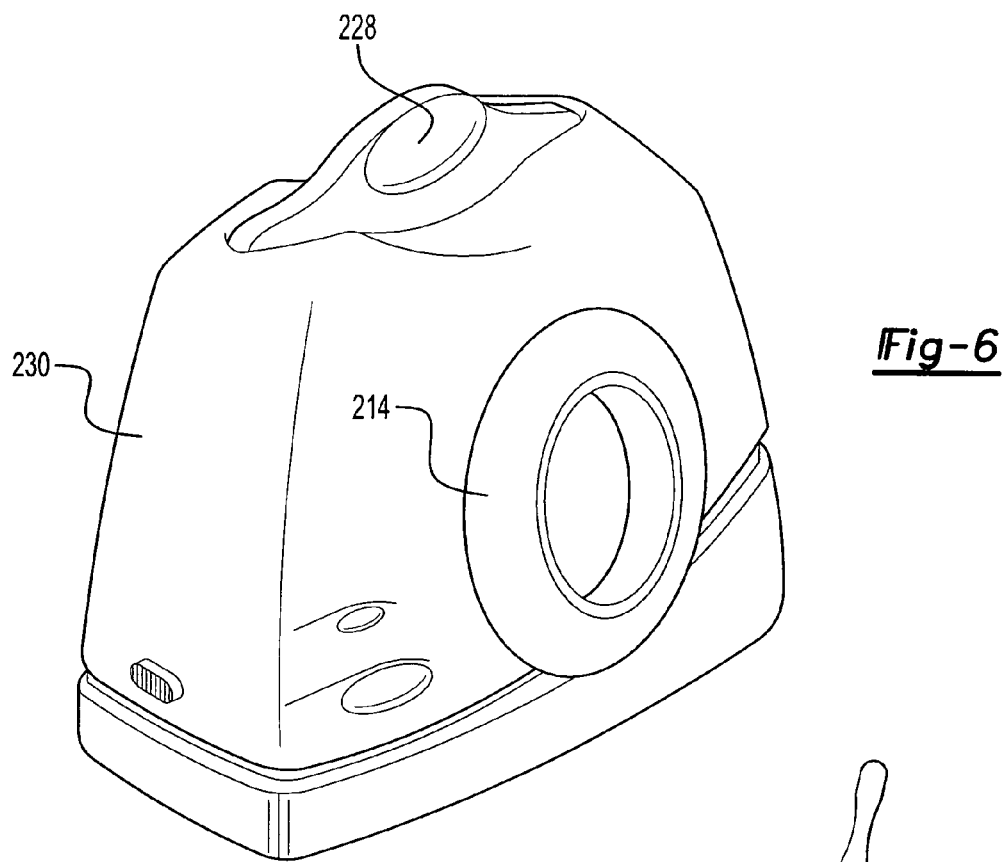
FIG. 6 is a perspective view of a third embodiment of a vortex generator.
Figure 7:
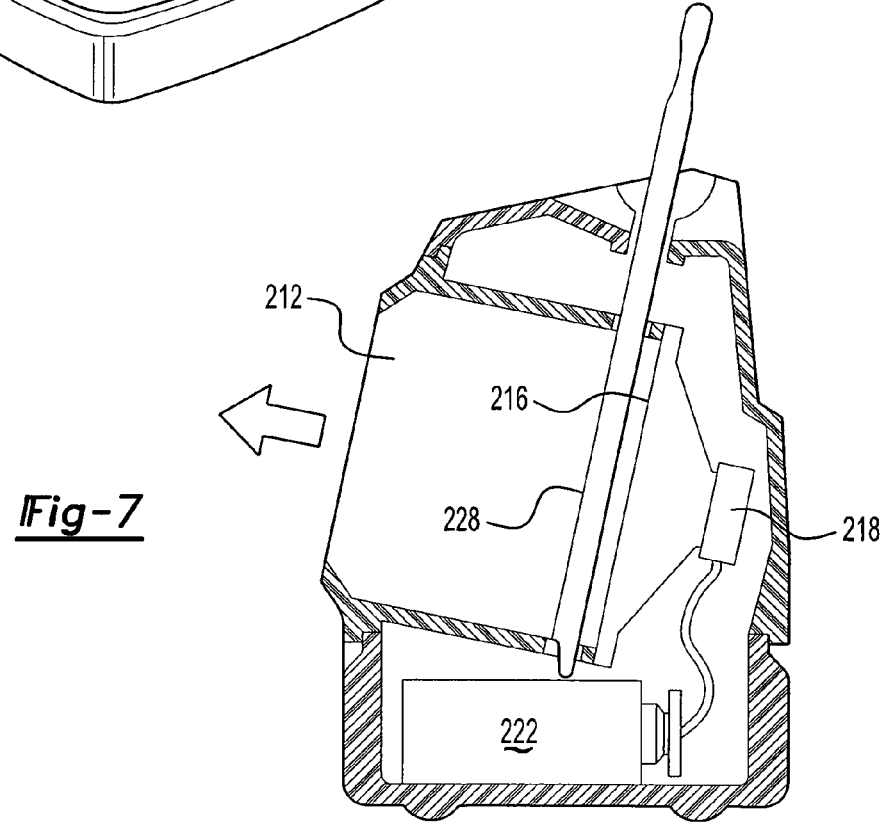
FIG. 7 is a cross-sectional view of the third embodiment shown in FIG. 6.

A third tabletop, portable embodiment of a vortex generator is seen in FIG. 6. The embodiment has a housing 230 receiving a refill 228 and having a vortex cone 214. The cross-sectional view of this tabletop embodiment is seen in FIG. 7 with a rechargeable battery 222 providing power to the vortex actuator 218 to move the diaphragm 216. The diaphragm 216 is at a terminal end of the vortex chamber 212 which leads to the vortex cone 214. The vortex chamber receives a membrane 228 impregnated with fragrance, repellant, insecticide or any other active substance wishing to be dispensed.

Figure 8:
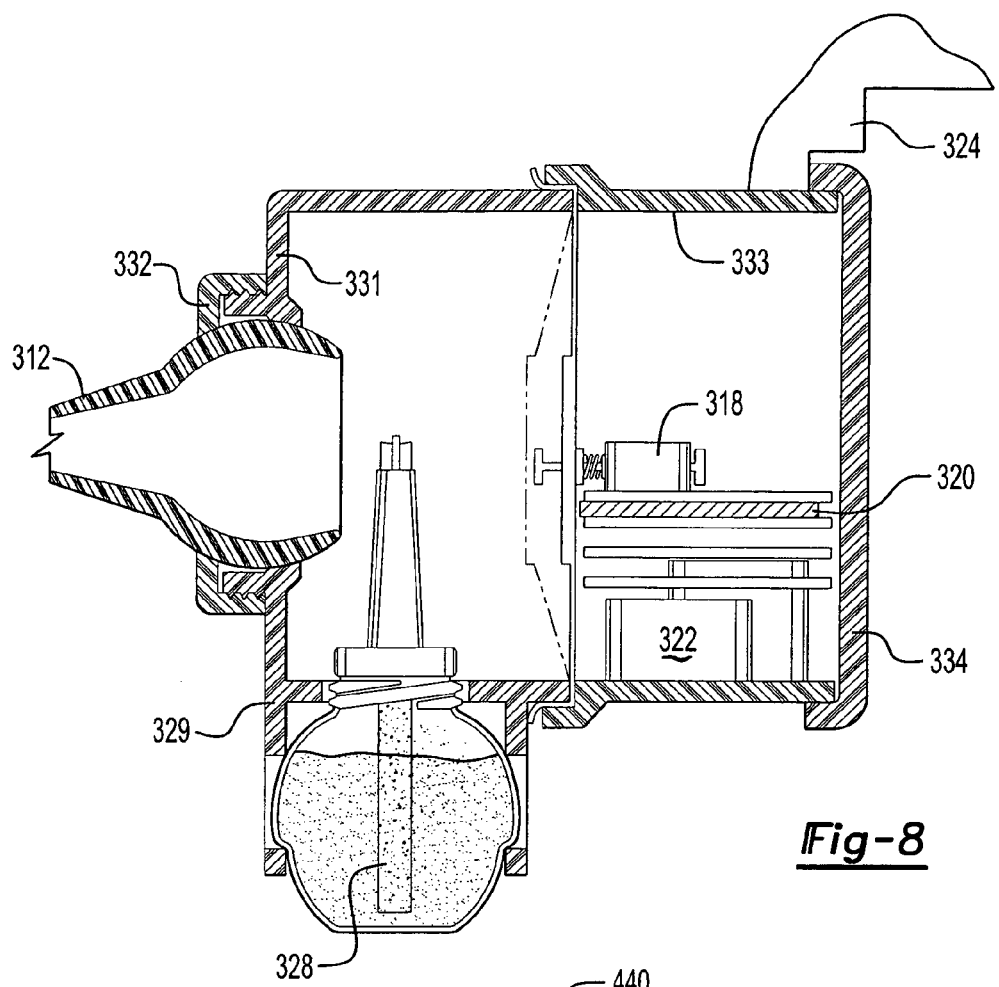
FIG. 8 is a cross-sectional view of a fourth embodiment of a vortex generator.

FIG. 8 shows a fourth embodiment of the vortex generator having a housing 330 formed by a front half 331 and a back half 332. The two halves retain a diaphragm 316. The front half forms the vortex chamber 312 and has a nozzle cap 332 holding a nozzle serving as a vortex cone 314. The vortex cone can be pointed in any desired direction and retained by tightening the nozzle cap 332. In this way, the bolus can be aimed without any other affect on the bolus. The back half of the housing accommodates the power supply 324 and battery 322. An actuator 318 controlled by a PC board 320 creates the waveform within the vortex chamber. The back half of the housing is sealed by a back cap 334. A retainer 329 holds a refill cartridge 328 in the vortex chamber 312.

Actuators can take one of several forms in the described embodiments. It is essential that the actuator reliably creates a mechanical disturbance that translates into a traveling pressure wave within the vortex generator to create the vortex bolus as it exits the orifice. Just as important is the ability for the actuator to move the diaphragm while only requiring minimum power. If the vortex generator is to be battery powered, the ability for a battery to power the generator for a long period of time is an advantage to the user.

Figure 9:
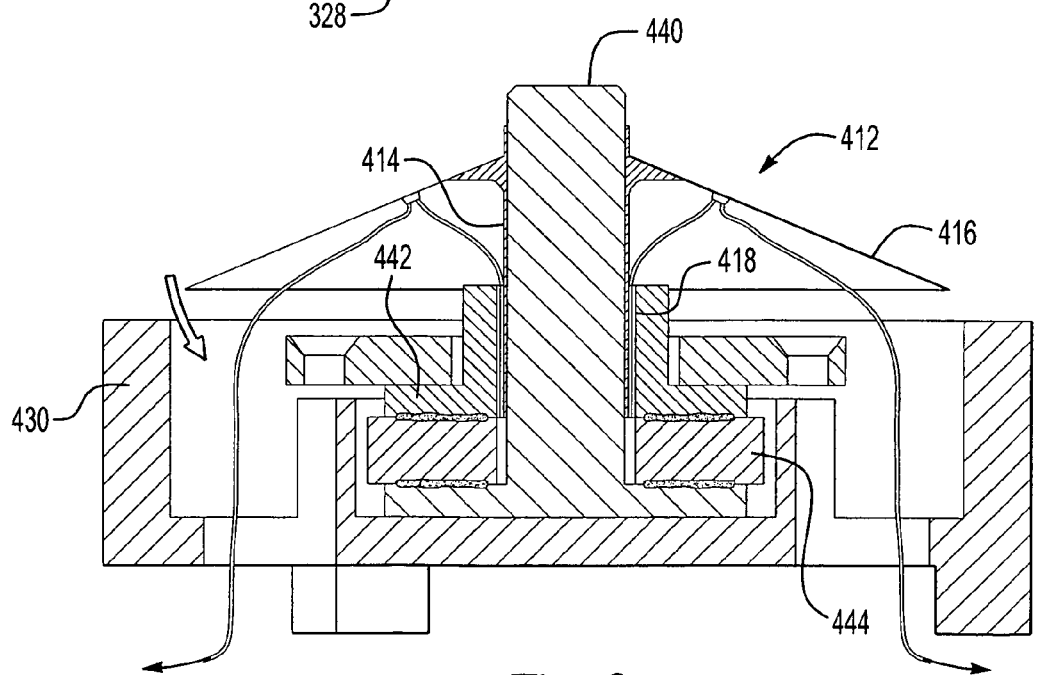
FIG. 9 is a cross-sectional view of a bobbin actuator.

FIG. 9 shows an actuator having a bobbin 412 formed by a cylinder 414 and attached diaphragm 416 made from paper, plastic, or similar lightweight but structurally sound material. A central iron piece 440 has a base and upstanding pedestal. The bobbin 414 fits about the pedestal and is surrounded by a coil 418 attached to a PCB controlling the current to the coil. Surrounding the coil is a second iron piece 442 and a ceramic magnet 444. The assembly is housed within a Delrin housing or suitable material. Wire is wound about the bobbin. When current is supplied through the wire, the oscillating movement of the pedestal causes the movement of the diaphragm to create a waveform. A vortex having an effective distance of five to seven feet is possible with this type of actuator.

Figure 10:
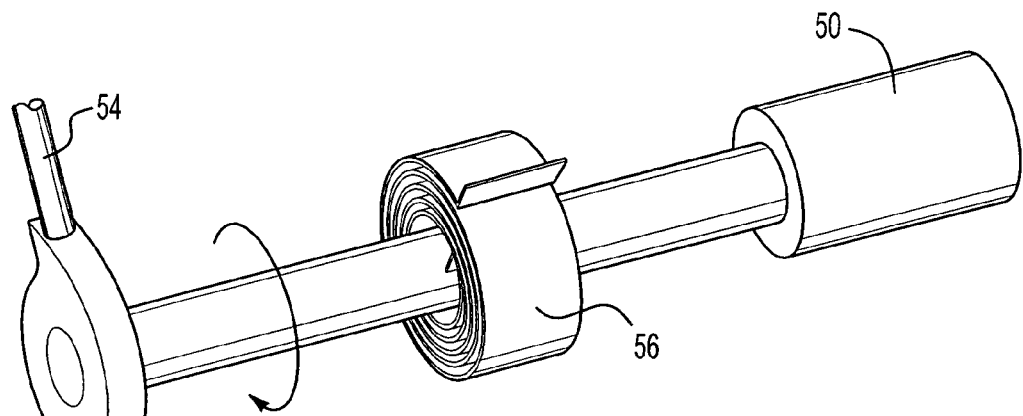
FIG. 10 is a view of a torsional spring and cam actuator.

FIG. 10 shows a second embodiment of a actuator having a motor 50 and a torsional spring 56 causing rotation of a cam 52. A cam follower 54 is moved in a reciprocating manner to cause corresponding movement of a diaphragm.

Figure 11A:
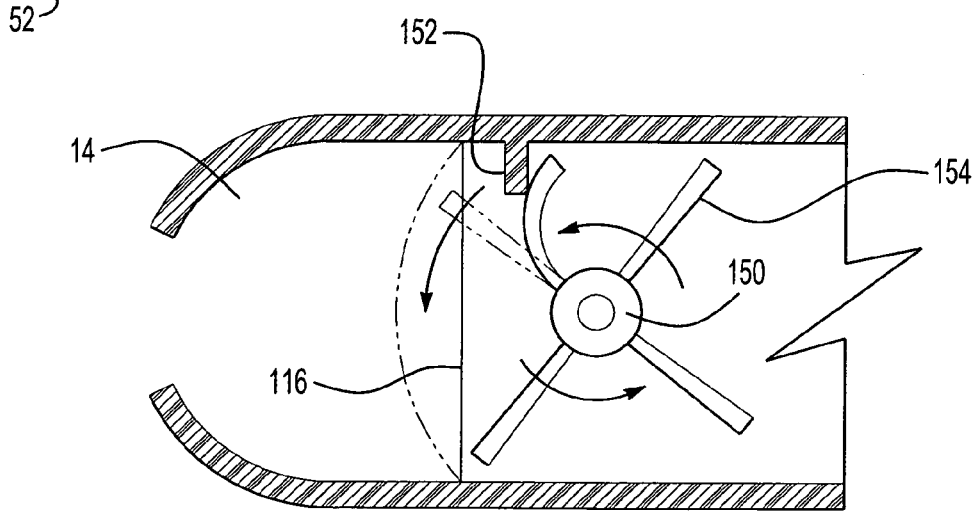
FIGS. 11a–b are views of hub and flapper actuators.

Yet another actuator shown in FIG. 11a includes a central hub 150 having a plurality of flappers 154 extending radially therefrom. Rotation of the hub 150 causes the flappers to abut a retainer 152 extending into the housing. When the flappers are free from the retainer, they strike the diaphragm 116 to cause the movement of the diaphragm and the creation of a waveform.

Figure 11B:
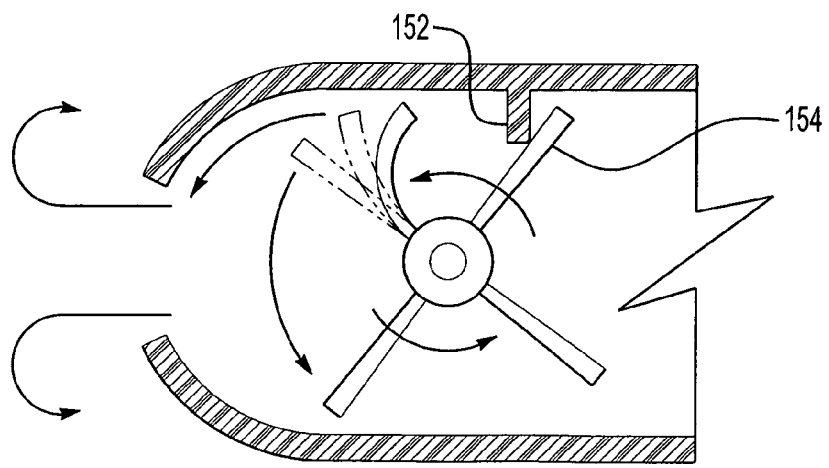

FIG. 11b shows a similar actuator eliminating the membrane. The flappers 154 are bent by the interference of the retainer 152. When the flappers clear the retainer, their resilience causes the flappers to straighten. This action causes a waveform and no diaphragm is needed.

Figure 12A:
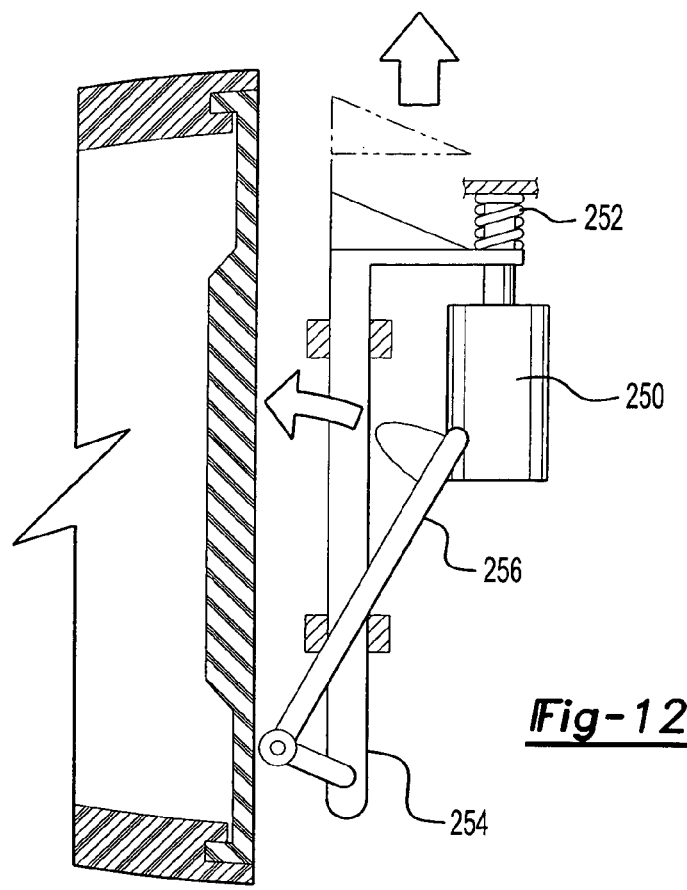
FIG. 12 is a view of a clapper with return spring actuator.
Figure 12A:
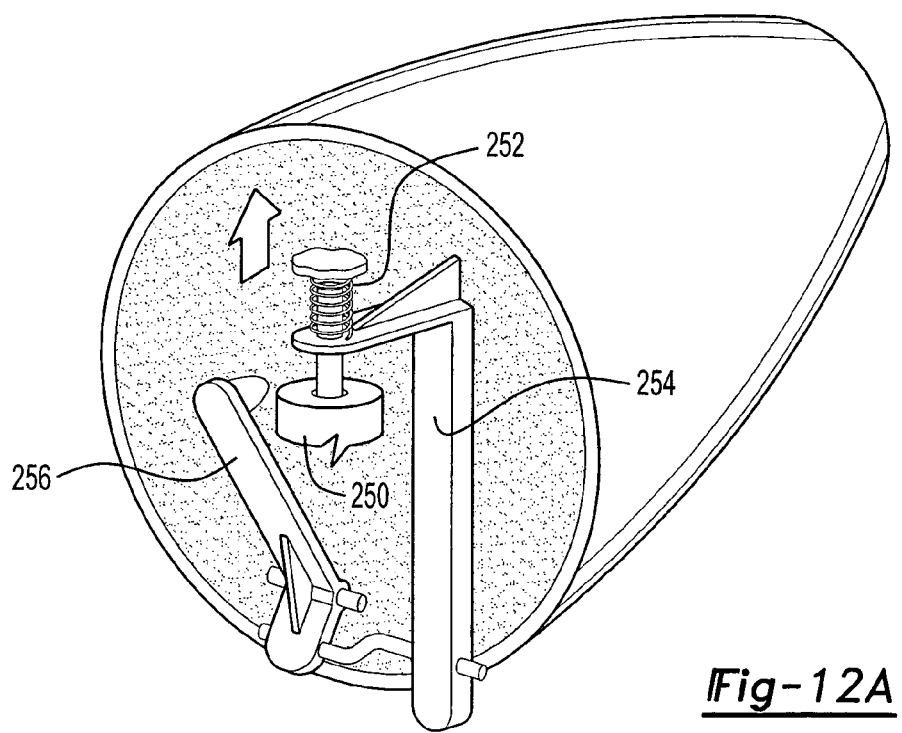

FIG. 12a discloses an actuator having a solenoid 250 and a return spring 252 acting upon a linkage 254 to create oscillating movement. The linkage 254 causes oscillating movement of a clapper 256 striking a diaphragm. FIG. 12b is a perspective view of this actuator.

Figure 13A:
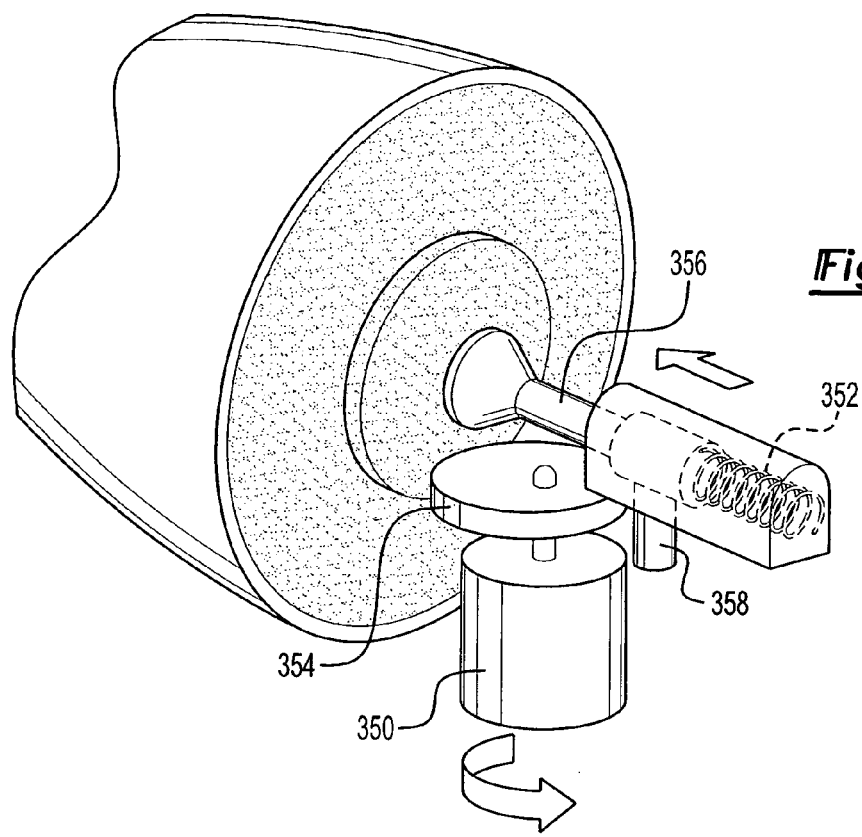
FIG. 13 is a view of a bolt action striker actuator.
Figure 13B:
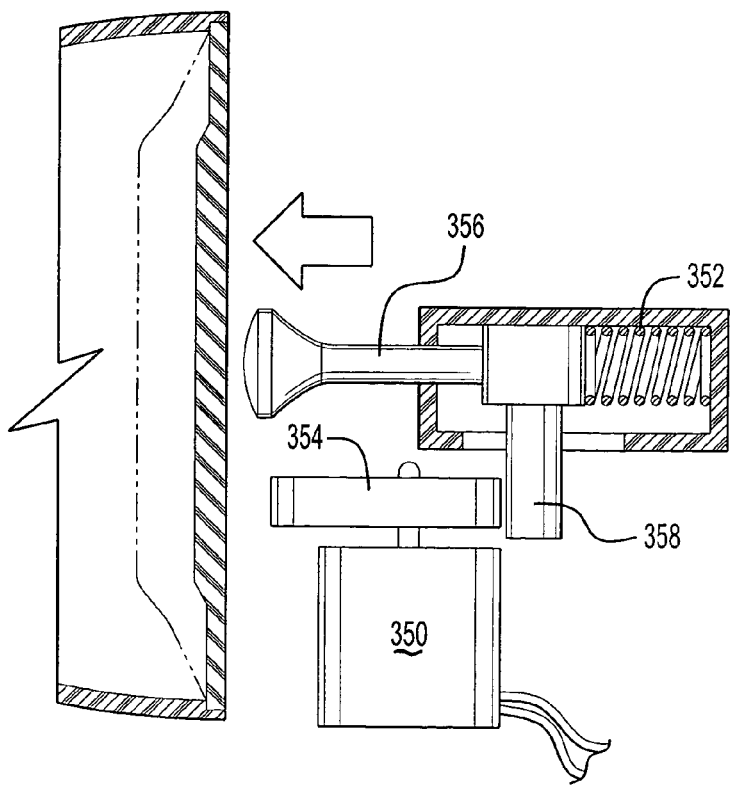

FIG. 13a is a perspective view of a bolt action actuator and FIG. 13b is a side view of this actuator. A motor 350 causes rotation of a cam 354. A striker 356 has a cam follower 358 bearing against the cam. Rotation of the cam causes oscillating movement of the follower. A return spring 352 insures the continued oscillating movement of the striker so that it may strike against the diaphragm.

Figure 14A:
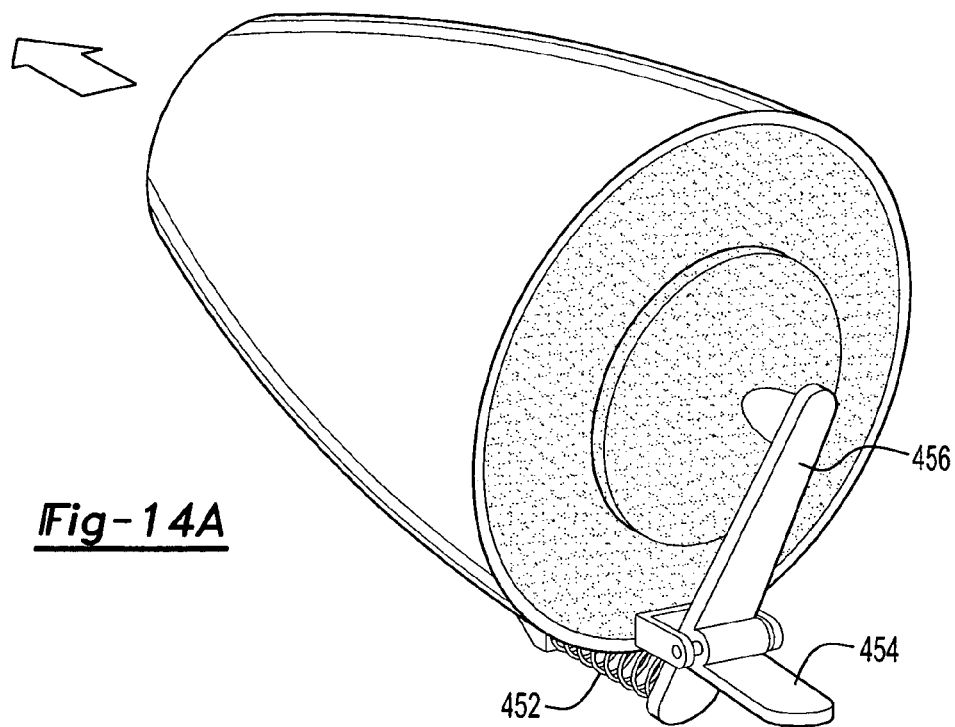
FIG. 14 is a view of a foot pedal actuator.
Figure 14B:
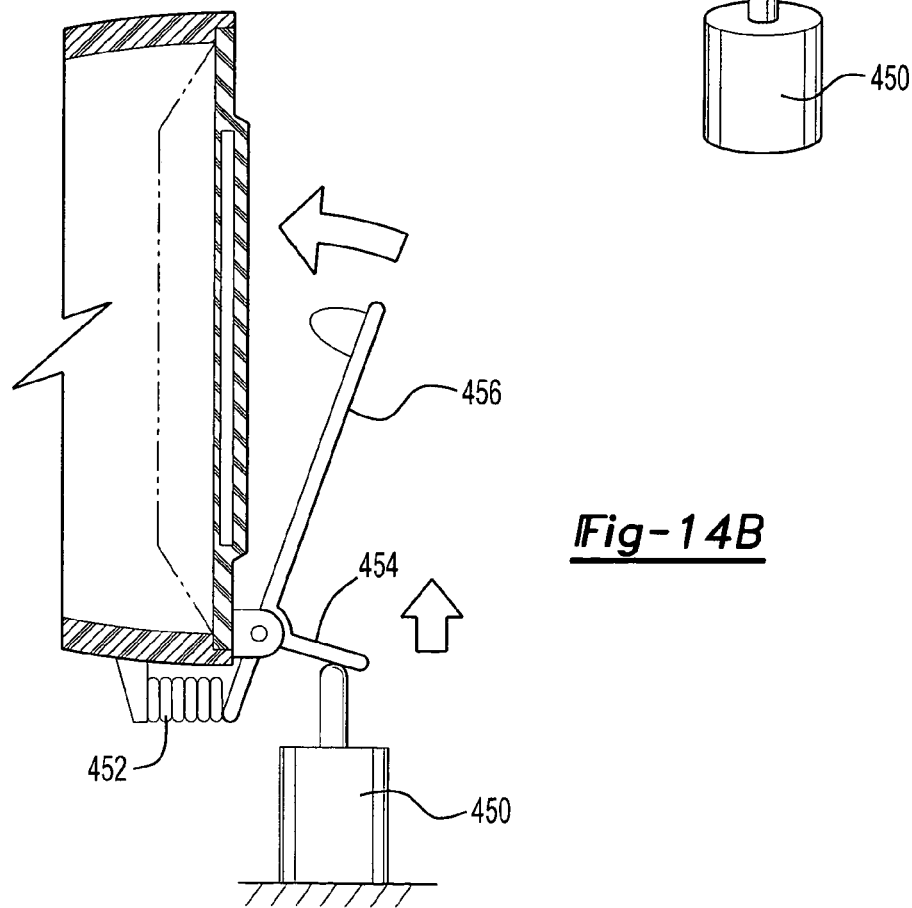

FIG. 14a is a perspective view of a foot pedal actuator and FIG. 14b is a side view of this actuator. A motor 450 bears against linkage 454 to cause movement of the striker 456. A return spring 452 is provided to insure the continued oscillating movement of the striker.

Figure 15:
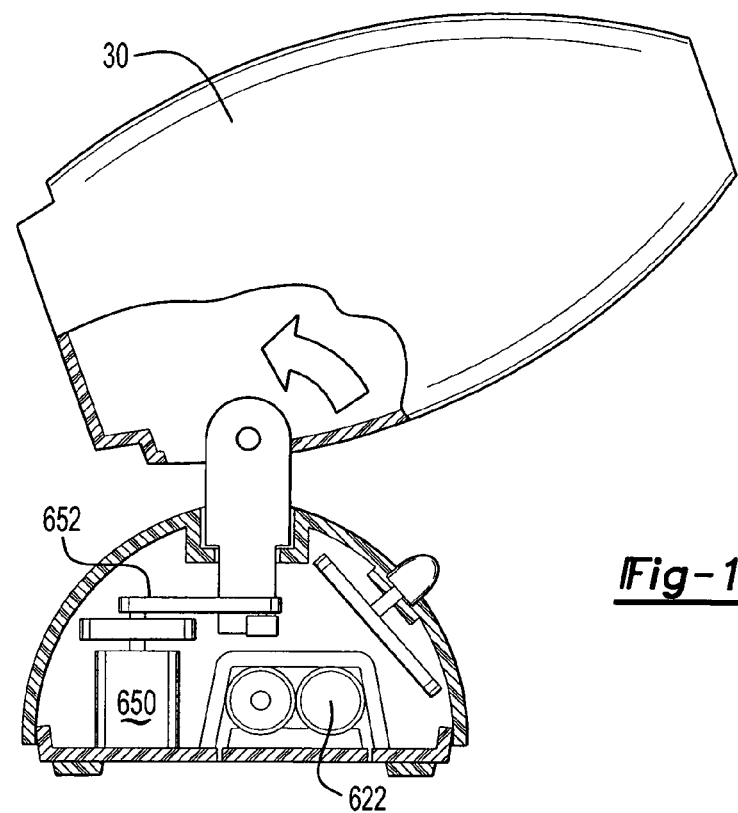
FIG. 15 is a cross-sectional side view of an oscillating mechanism.
Figure 16:
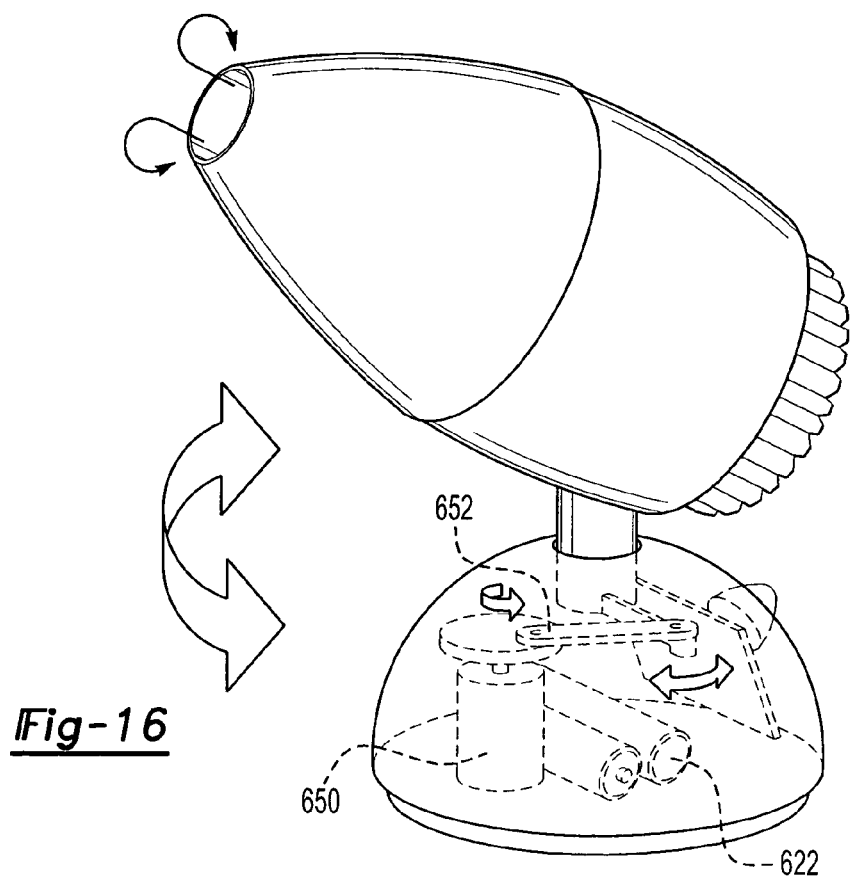
FIG. 16 is a perspective view of an oscillating vortex generator with a section of the base broken away for clarity purposes.

An additional feature of a vortex generator is the ability to directionally vary the generated vortex. It is beneficial to provide the housing with an oscillating motion so that the vortices can be spread throughout the desired affected area. An oscillating mechanism is shown in side view in FIG. 15 and perspective view in FIG. 16. A motor 650 drives an oscillating linkage 652. Rotation of the linkage causes oscillating of the vortex generator. The motor is powered by a battery 622, but may be powered by other means.

Figure 17:
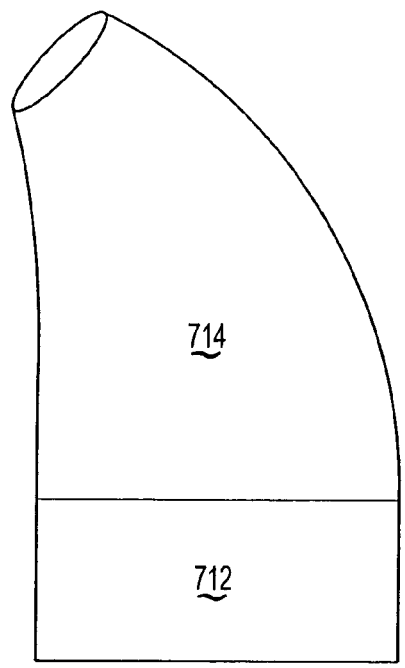
FIG. 17 is a side view of a preferred embodiment of the invention.

FIG. 17 is a side view of a preferred embodiment of the vortex generator having a vortex chamber 712 and vortex cone 714. The actuator and diaphragm may be mounter in either the chamber or cone. The chamber and cone together define a cone having a curved longitudinal axis. The result is an outlet at an angle to the bottom of the chamber, as shown. As with all embodiments of the vortex cone, any of the disclosed actuators for the diaphragm may be used to create the waveform.

Figure 18:
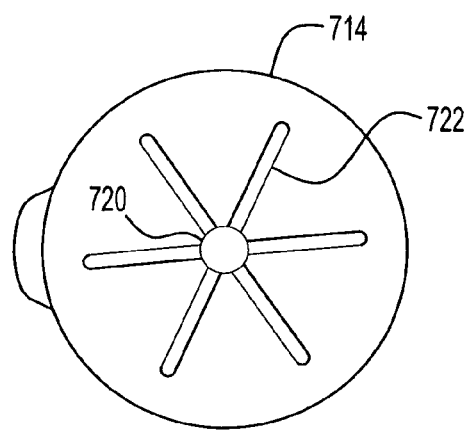
FIG. 18 is a bottom view of the vortex cone having the active insert.

FIG. 18 shows a bottom view of the vortex cone with an active refill in the form of a hub 720 and spokes 722. The spokes are made of absorbent material to contain the substance to be dispensed. As the pressure wave passes through the vortex cone, it passes by the spokes and picks up the substances from the spokes.

Figure 19:
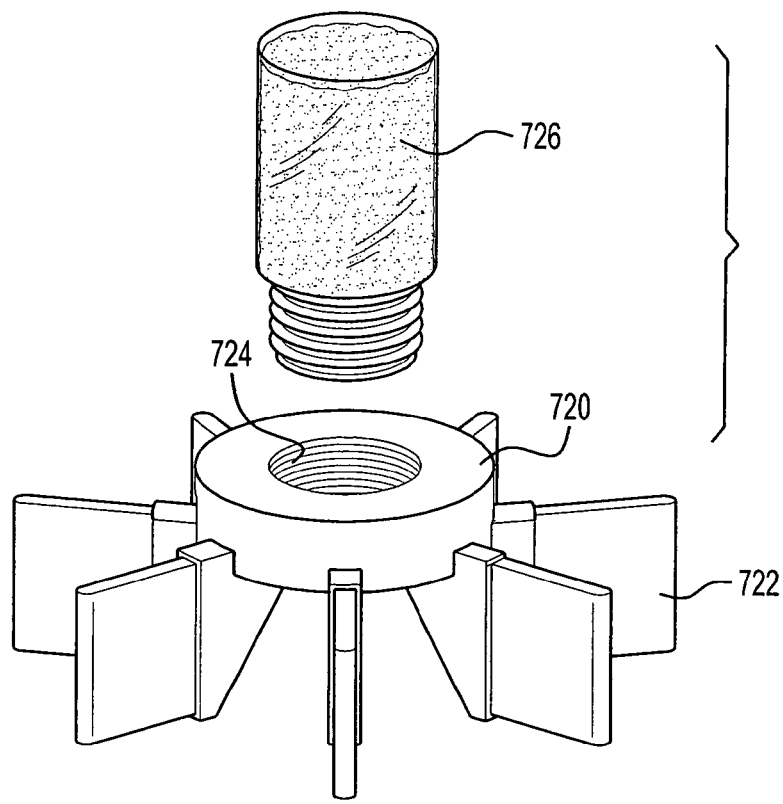
FIG. 19 is a perspective view of the active insert of FIG. 18.

FIG. 19 is a perspective view of the active insert seen in FIG. 18. The active insert has a hub 720 with a plurality of spokes 722 extending therefrom. The hub 720 has a central recess 724 to receive a bottle 726 containing the active liquid. The hub and spokes are retained within the vortex chamber in any suitable manner.

Figure 20:
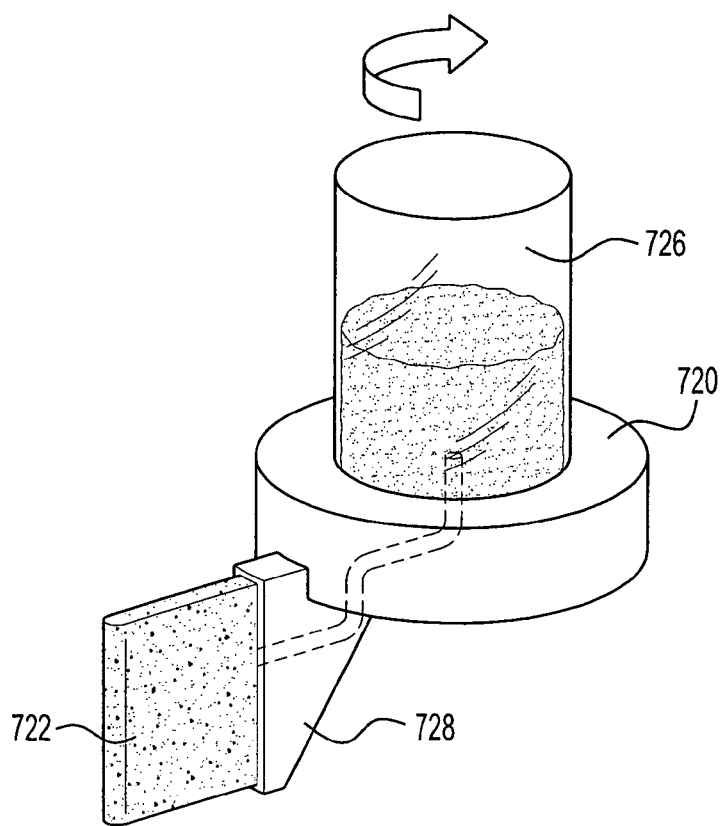
FIG. 20 is a perspective view of the active insert of FIG. 18 with spokes removed for clarity.

The bottle 726 is retained within the recess 724 by conventional means such as threads. When the central recess 724 fills with liquid to cover the opening of this bottle 726, no further liquid can escape the bottle until the level falls below the bottle opening, allowing air into the bottle. Details of this active can be seen in FIG. 20. In this view, all but one spoke have be removed for clarity purposes. In this view the bottles 726 is fully engaged in the hub 720. As can be seen in this Figure, each spoke has depending retainer 728 provided with a slot to receive the spoke 722.

Each retainer 728 has a passageway leading to the recess 724 to receive liquid from the bottle 726. The hub need not have a recess and bottle but, if not, the active insert will need to be replaced once the initial charge of active is dissipated from the absorbent material. Alternatively, the spokes may be made of a gel of active material rather than absorbent material.

An advantage of the hub and spokes arrangement is the large surface area of active. This large surface area creates a high concentration of active within the vortex cone which is especially beneficial to dispense insecticides in an effective amount.

FIG. 21 shows a cross section of the vortex generator of FIG. 17 having a diaphragm 716 creating a waveform in vortex cone 714. Extending from the inner sidewall of the vortex cone 714 is bracket 718 for retaining a bottle refill 730. The bottle refill 730 has a wick 732 extending into the active contained in the bottle refill 730 and outwardly above the bracket 718. The wick is saturated with the active and is able to create a concentration in the air proximate the outlet of the vortex cone 714. The waveform generated by diaphragm 716 carries the active concentration out of the outlet where, upon leaving the outlet, the waveform is transformed into a vortex and the bolus carries the concentration produced by the wick 732. It has been found that creating the concentration near the outlet allows the concentration to become entrapped within the vortex. Because the waveform does not travel far after picking up the concentration before developing into a vortex, a high percentage of the concentration is successfully trapped by the vortex.

FIG. 22 shows an alternative method for creating a concentration proximate the outlet of the vortex cone 714. In this embodiment, the end of the nozzle and refill are combined and releasably attached to the end of the vortex cone 714. The refill has a ring 734 attachable to the end of the vortex cone 714 and carrying refill 736. The refill 736 can be a gel, wick or saturated sponge or any other material capable of producing a concentration of the active in the air at the outlet of the vortex cone 714. The waveform generated by the diaphragm 716 carries the concentration out of the vortex cone 714 and upon exiting the cone creates a vortex entraining the concentration as a bolus. When the active 736 is exhausted, the ring 734 is detached from the vortex cone 714 and a new ring having a fresh supply of active is attached.

Figure 23:
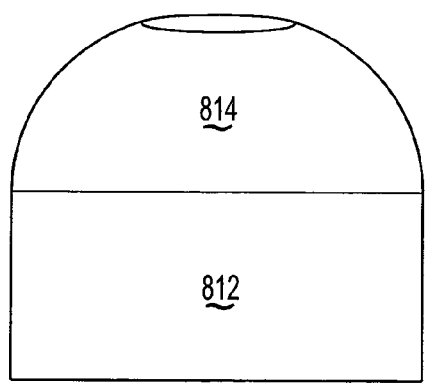
FIG. 23 is a side view of the preferred embodiment of the invention.
Figure 24:
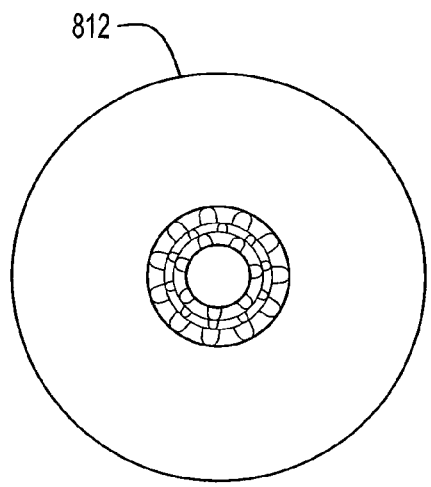
FIG. 24 is a bottom view of the vortex cone having the active insert.

FIG. 23 is a view of another preferred embodiment of the vortex generator having a vortex chamber 812 housing the diaphragm and diaphragm actuator and a vortex cone 814. The bottom view of the vortex cone of FIG. 24 shows the active refill in the form of concentric rings separated from one another by corrugations. The pressure wave passing through the vortex cone, passes through the active refill and picks up the active substance from the refill.

What is claimed is:

1. A vortex generator for dispensing actives, comprising
   a vortex chamber,
   a vortex element connected to said vortex chamber and having an orifice,
   a bobbin housed within said vortex chamber for creating a pressure wave within said vortex chamber, said pressure wave traveling through said vortex element and exiting through said orifice as a vortex,
   said bobbin comprising a cylinder and a diaphragm extending from said cylinder, and
   a coil for causing axial movement of said cylinder.

2. The vortex generator of claim 1, further comprising a printed circuit board for controlling said coil.

3. The vortex generator of claim 1, further comprising an insert containing an active substance to be dispersed via said vortex generator.

4. A vortex generator for dispensing actives, comprising
   a housing
   a vortex chamber in said housing,
   a vortex element connected to said vortex chamber and having an orifice,
   a waveform generator in said vortex chamber for creating a waveform and forming a vortex when exiting said vortex element orifice, said waveform generator comprising a diaphragm and an actuator in said housing for causing movement of said diaphragm.

5. The vortex generator of claim 4, wherein
   said diaphragm actuator comprises a torsional spring and cam, said cam contacting said diaphragm.

6. The vortex generator of claim 4, wherein
   said diaphragm actuator comprises a motor driving a cam and a striker having a cam follower engaging said cam, said striker contacting said diaphragm.

7. The vortex generator of claim 4, wherein
   said diaphragm actuator comprises a hub having at least one flapper extending radially outwardly from said hub, said flapper contacting said diaphragm.

8. The vortex generator of claim 4, wherein
   said diaphragm actuator comprises a foot pedal actuator having a striker, said striker moved toward the diaphragm by a motor and away from said diaphragm by a return spring.

9. The vortex generator of claim 4, wherein
   said diaphragm actuator comprises a solenoid and return spring causing oscillating movement of a linkage, said linkage causing a clapper to strike said diaphragm.

10. The vortex generator of claim 4, further comprising an active substance housed within said vortex element creating a concentration of said active substance.

11. The vortex generator of claim 4, wherein
    said vortex element orifice in said housing communicate with the ambient environment.

* * * * *